United States Patent [19]

Schenck et al.

[11] Patent Number: 4,693,249
[45] Date of Patent: Sep. 15, 1987

[54] ANASTOMOSIS DEVICE AND METHOD

[76] Inventors: Robert R. Schenck, 1100 N. Lake Shore Dr., Aptmt. 33A, Chicago, Ill. 60611; Harry P. Weinrib, 2644 West Estes Ave., Chicago, Ill. 60645

[21] Appl. No.: 817,825

[22] Filed: Jan. 10, 1986

[51] Int. Cl.$^4$ .............................................. A61B 17/04
[52] U.S. Cl. .................................. 128/334 R; 128/343
[58] Field of Search ............... 128/334 R, 334 C, 341, 128/343, 345

[56] References Cited

U.S. PATENT DOCUMENTS

| | | | |
|---|---|---|---|
| 2,453,056 | 11/1948 | Zack | 285/242 |
| 3,254,650 | 6/1966 | Collito | 128/334 C |
| 3,316,914 | 5/1967 | Collito | 128/334 C |
| 3,908,662 | 9/1975 | Razgocov et al. | 128/334 C |
| 4,055,186 | 10/1977 | Leveen | 128/334 C |
| 4,352,358 | 10/1982 | Angelchik | 128/334 R |
| 4,470,415 | 9/1984 | Wozniak | 128/334 R |
| 4,474,181 | 10/1984 | Schenck | 128/334 R |
| 4,523,592 | 6/1985 | Daniel | 128/334 C |

FOREIGN PATENT DOCUMENTS 2101284  7/1971  Fed. Rep. of Germany .
1181563  2/1967  United Kingdom .

OTHER PUBLICATIONS

D. A. Donetskii, "A New Method For A Circular Vascular Suture", (Dec. 1956, Fksperim Khirur. 1.), pp. 53-59.

Nakayama, et al., Surgery, Dec. 1962, pp. 918-931.

Primary Examiner—Albert J. Makay
Assistant Examiner—David W. Westphal
Attorney, Agent, or Firm—Fitch, Even, Tabin & Flannery

[57] ABSTRACT

Ring-shaped anastomosis devices have outwardly extending protrusions for impaling a pair of living vessel ends thereon without the need for sutures. A first vessel end is inserted through a central opening of a device, everted around the end of the device and impaled on the protrusions; then a second vessel end is drawn over the everted first vessel end and similarly impaled on the protrusions. To facilitate impaling the vessel ends on the protrusions and to minimize tearing of the vessel walls during the impaling process, the devices are incomplete rings, each having a first ring end and a second ring end. A device has a contracted configuration in which it is maintained during the impalation process to hold the protrusions relatively close to each other and an expanded configuration in which it is maintained subsequent to joining the vessel ends thereto to hold the vessels in a slightly stretched condition and with their intima apposed.

20 Claims, 19 Drawing Figures

ANASTOMOSIS DEVICE AND METHOD

ANASTOMOSIS DEVICE AND METHOD

The present invention is directed to methods and apparatus for anastomosing ends of living vessels and more particularly to anastomeses effected using encircling devices.

BACKGROUND OF THE INVENTION

Among the important and time comsuming tasks in surgical procedures is the anastomosis or joining of severed blood vessels, and the success of a surgical procedure may depend on the degree of circulation which is restored through such anastomoses. Conventional anastomosing of blood vessels using sutures is after a tedious procedure, particularly in blood vessels of small diameter, including blood vessels less than one mm. in diameter. Conventional blood vessel suturing techniques are time-consuming, extending the duration of a surgical procedure and successful anastomosing of blood vessels is highly dependent on the proper placement of sutures by the surgeon. Particular difficulty is often encountered in anasotomosing children's vessels which are small and prone to spasm.

Blood vessels of all but the largest size, i.e., the aorta and vena cava in humans, have a naturally occuring contractility, identified as circumferential compressive stress, that resists dilation. These forces become proportionately larger as the vessel diameter decreases and the relative wall thickness increases. Radial tethering forces of tissues do exist around the vessel, but these are of lesser significance than longitudinal vessel motion tethering.

Successful suturing of blood vessels does not assure their continued patency, i.e., their ability to conduct blood flow. Thrombosis (clotting of blood) may act to block blood flow through an anastomosed vessel. In addition to inaccurate placement of sutures, several other factors—spasm, stenosis, and microclamp damage—may be additive in causing thrombosis after microvascular repair. It has been found that continuity of flow during the first twenty minutes after anastomosis is critical in preventing thrombus formation. It has also been found that platelet aggregation, and later resolution occurs in the first several hours after a microvascular anastomosis.

To aid in anastomosing blood vessels, implantable devices which connect severed ends of blood vessels have been described previously, e.g., U.S. Pat. Nos. 3,254,650 and 4,055,186, British Pat. No. 1,181,563, German Fed. Rep. Pat. No. 2,101,282 and Nakayama et al. *Surgery* December 1962, pp. 918–931. Devices have also been described for everting severed ends of blood vessels to facilitate their suturing, e.g., U.S. Pat. No. 2,180,337.

Our U.S. Pat. No. 4,474,181 describes an external ring to which a pair of vessels having prepared openings may be tethered with sutures so as to hold their intima in fluid-tight apposition. This device provides good assurance or patency by maintaining the lumen of the vessels in an expanded condition at the anastomosis site.

There are advantages to avoiding the use of sutures entirely, particularly for the smaller vessels. In a typical surgical procedure, a large number of small vessels may require anastomosis, and cumulatively the time spent anastomosing these vessels contributes significantly to the time needed to complete the surgical procedure. A. D. Donetskii, *Eksperim Khirur.* 153–59 (1956) describes an anastomosis ring having outwardly extending protrusions which are used to impale a first vessel end that is inserted through the ring opening and then everted around the outside surface of the ring and a second vessel end which is then draped over the everted vessel end and impaled on the protrusions.

Some of the smaller and weaker vessels tend to tear after the vessel has been impaled on two of the protrusions on an anastomosis ring and the vessel is being stretched to impale on the third of the protrusions. With appropriately proportioned rings having inside surfaces slightly smaller than the unstressed or relaxed exterior diameter of the vessel ends and exterior diameters slightly larger than the relaxed exterior diameter of the vessel, there is seldom a problem in impaling the vessel on the first two of the protrusions, but tearing often occurs when impaling the vessel on the third. If vessel tearing is avoided during the impaling process, a stable, patent anastomosis is generally affected.

It is a general object of the invention to provide a new and improved sutureless anastomosis device in which first and second living vessel ends are impaled on points on an anastomosis ring which has been contracted to a smaller size and which is then shifted to an enlarged size to enlarge the lumens of the vessel ends. More particularly, it is an object to provide such a ring which is contracted in size to miminize tearing of vessel ends during the extension of the vessel ends over the impaling points on the ring.

The invention provides a substantially encircling member in the form of an incomplete ring having an interior surface defining a central opening, an exterior surface, a first ring end and a second ring end and three or more protrusions extending radially outward from the exterior surface for hooking or impaling a pair of prepared ends of living vessels. The incomplete ring is deformable between a first contracted state or configuration and a second expanded state or configuration, and means for maintaining the ring in at least one of said states. With the ring in the first contracted state, a first prepared end of a vessel is drawn through the ring, everted around the end of the ring and along the outside surface where it is impaled on each of the protrusions, in turn. Next, the second end is drawn over the everted and impaled first vessel end and impaled on each of the protrusions, in turn, thereby bringing the intima of the vessels into sealing apposition. With both vessel ends impaled on the ring, the ring is then expanded to its second expanded state, where it is maintained, holding the apposed vessel ends in a slightly stretched state as they heal.

These and other objectives and advantages of the invention will become more apparent from the following detailed description of the invention in reference to the accompanying drawings in which:

DETAILED DESCRIPTION OF THE DRAWINGS

FIG. 1a is a side view, partially cut away, of a prior art sutureless anastomosis device having a pair of vessel ends anastomosed thereby;

FIG. 1b is a side view of such a prior art device in which an everted first vessel end is being attached to the prior art device of FIG. 1a;

FIG. 1c is a diminutive end view of the prior art device;

FIG. 2a is an end view of an anastomosis device, embodying various features of the invention, in a first coiled configuration;

FIG. 2b is an end view of the device of FIG. 2a in a second expanded configuration;

DETAILED DESCRIPTION OF THE PREFERRED EMBODIMENT

Figures 1A, 1B, 1C, 2A, 2B:
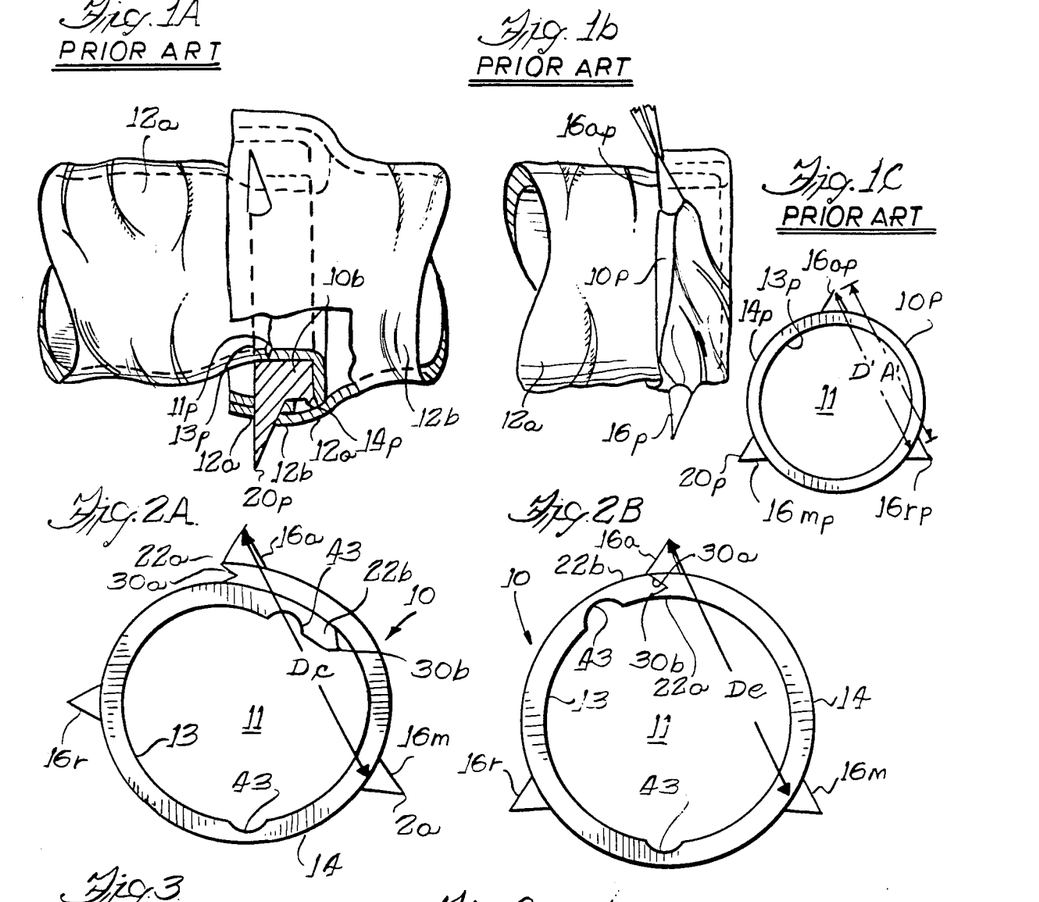

Illustrated in FIG. 1a is a prior art annular device 10p having a pair of vessel ends 12a, 12b anastomosed thereby. The device 10p with reference to FIG. 1c is in the form of a complete ring having an interior surface 13p defining a central opening 11p, an exterior surface 14p and three points or protrusions 16rp, 16mp, 16ap extending radially outward of the exterior surface. The first vessel end 12a is extended through the central opening 11p, everted around the end of the device 10p, and impaled on each of the hooking protrusions 16rp, 16mp, 16ap at generally evenly spaced circumferential locations along the vessel wall. (In the prior art device, there is no actual difference between the protrusions, and the arbitrary labelling is for purposes of discussion. The protrusion 16ap, for purposes of discussion, is the last protrusion on which a vessel end is impaled). The second vessel end 12b is drawn over the everted first vessel end 12a and likewise impaled on each of the hooking protrusions, thereby bringing the intima 18 of the two vessel ends into sealing apposition. This device 10p has important advantages in that it can be used to quickly anastomose vessels, including very small vessels, e.g., 0.5 mm in diameter and even smaller. Furthermore, the device holds open the lumen of the vessel ends, helping to ensure that the anastomosis remains patent.

It is found that such devices 10p are most useful if their exterior diameter is slightly larger than the relaxed exterior diameter of the vessel ends being joined, resulting in the anastomosed vessel ends being radially stressed outward along the exterior surface 14p of the device. To accommodate the necessary radial thickness of the device, the interior diameter is typically equal to the natural, relaxed exterior diameter of the vessel ends; thus, the diameter of the vessel passageway that is maintained by the eversion of the first vessel end 12a around the device 10p ensures patency and good fluid flow. The protrusions 16rp, mp, ap are intended to penetrate both vessel ends 12a, 12b, securing them to the ring, and the tips 20p of such protrusions typically extend along a circular locus which is between about 1.5 and about 2.0 times the relaxed exterior diameter of the vessel ends.

It has been found that initially securing the vessel ends 12a,b to such a device 10p may cause tearing of the vessel ends, particularly when drawing one of the vessel ends over the last protrusion 16ap. Illustrated in FIG. 1b is a first vessel end 12a which is extended through the prior art device 10p, everted around the end of the device, impaled on two of three protrusions 16rp, 16mp and is being drawn over the end of the third protrusion 16ap. Generally, it has been found that there is little trouble drawing the vessel end over the first two protrusions; however, when drawing the vessel over the third protrusion, which represents the point of maximum vessel stretching, there is a tendency to tear the vessel end. If drawing of the vessel end over the third protrusion is accomplished without tearing, the natural contraction of the vessel end draws the vessel end along the exterior surface 14p of the ring, where it is less stretched and remains without danger of tearing.

The degree of stretching which a vessel end can withstand depends on the type and nature of the vessel. The most common use of the device described herein will be for anastomosing blood vessels; however, their use for other living vessels, such as fallopian tubes, vas deferens, nerve sheaths, ureters, etc., is contemplated. Even vessels for the same general purpose, e.g., different blood vessels, may have substantially different tear strengths and elasticity, depending, for example, on the amount of muscle tissue surrounding the vessels. The devices according to the present invention are most advantageous for joining vessels that are most susceptible to tearing; however, advantages for even stronger vessels can be appreciated, such as allowing the use of larger devices that provide a larger vessel passageway after anastomosis.

In accordance with the present invention, an anastomosis ring or device 10 is in a smaller size or contracted state when the blood vessels are being interconnected and impaled on the points and then the ring is expanded to a larger size or state to open more fully the vessel lumens for liquid flow therethrough. The illustrated and preferred ring-like bodies are biased to one state, either the expanded or contracted state, and the surgeon shifts them to their other state, either expanded or contracted. For instance, the ring-like body 10 shown in FIG. 2A is biased to its smaller diameter, contracted state prior to having the blood vessels attached to its points 16a, 16m, 16r and the surgeon will expand the ring and bring its ends 22a and 22b into locking engagement to hold the ring-like body in its expanded state. Conversely, as will be explained in connection with FIGS. 10a, 10b, and 11a and 11b, the ring-like body is biased to the expanded condition, FIGS. 10b and 11b; and, after surgeon has attached the vessels to the points with the ring-like body in its contracted state, a means interconnecting the ring ends is disconnected to allow the resilience of the plastic body to expand the size of the ring. Thus, it will be seen that the ring-like body is in a smaller size contracted state to lessen the distance that the vessel walls must be stretched by the surgeon when impaling the walls on the points; and, after such impaling, the ring-like body is shifted to the expanded state increasing the lumen in the vessels.

In each of the preferred and illustrated embodiments, a complete ring is formed in one of its two states with ends of the ring abutted and interconnected. In the other of its states, the ends of the ring are separated, an incomplete ring shape is formed. As will be explained hereinafter, the surgeon will do the shifting of the ring ends between these two states.

In accordance with the present invention and with reference to FIGS. 2a and 2b, the device 10 is provided for anastomosing a prepared first vessel end 12a to a prepared second living vessel end 12b (FIG. 7) without the use of sutures, the device being constructed so as to minimize the chance of tearing the vessel ends as they are anastomosed by the device. The device 10 is a member in the form of an incomplete ring having an interior surface 13 which defines a central opening 11, an exterior surface 14, a first ring end 22a, a second ring end 22b, and two or more protrusions (three 16a, 16m, 16r being shown) extending radially outward of the exterior surface 14 for impaling and thereby securing a pair of vessel ends 12a, 12b to the device. The device or ring 10 has a first contracted state or position (FIG. 2a) which facilitates joining of the vessel ends thereto in a manner that avoids vessel tearing and a second expanded state or position (FIG. 2b) for maintaining the vessel ends 12 joined thereto in a slightly stretched condition. First means are provided for maintaining the vessel ends in the contracted configuration as the vessel ends are joined thereto, and means 30a, 30b are provided for maintaining the vessel ends in the expanded condition. Depending upon the particular construction of the ring 10, or 110, e.g., the embodiments shown in FIGS. 2a, 2b or FIGS. 10a, 10b, the controlled or the expanded configuration may be the natural unstressed state of the incomplete ring, whereas the other configuration is maintained by mechanical means.

Figure 6:
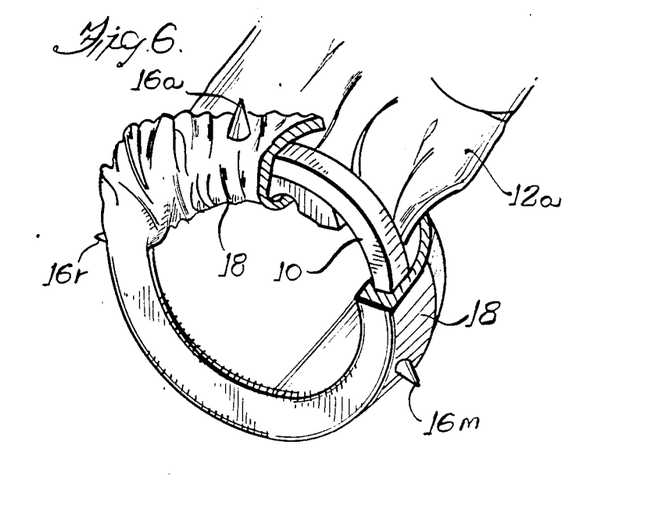
FIG. 6 is a cut-away perspective view of a first living vessel end as it is initially attached to the device of FIG. 2 in its coiled configuration.
Figures 7, 8:
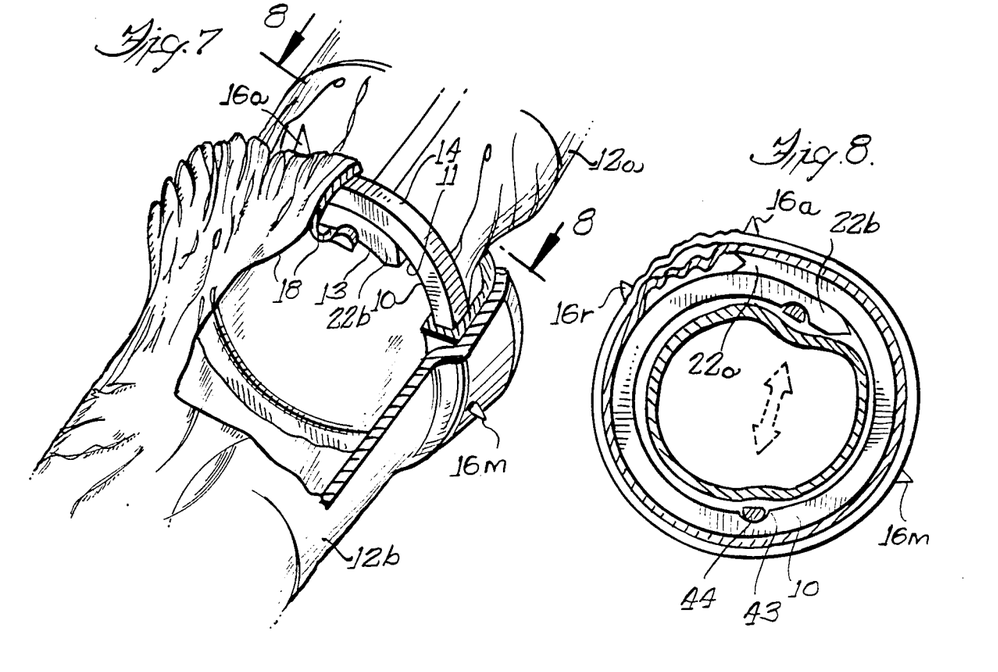
FIG. 7 is a cut-away perspective view of a pair of vessel ends as they are initially attached to the device of FIG. 2 in its coiled configuration and showing a tang of a reverse-action forceps being used to manipulate the device from its coiled to its expanded configuration.
FIG. 8 is a view taken along FIG. 8—8 of FIG. 7.
Figures 9, 10A:
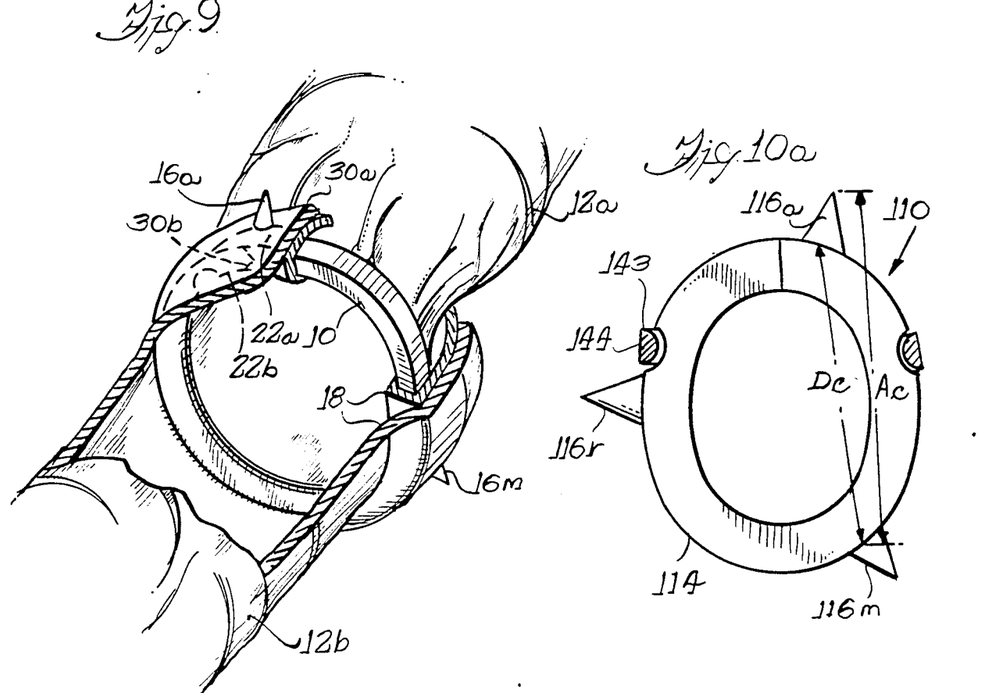
FIG. 9 is a cut-away perspective view of a pair of vessel ends anastomosed by the device of FIG. 2 in its expanded configuration.
FIG. 10a is an end view of an anastomosis device, representing an alternative embodiment of the present invention, in a first coiled configuration and showing tangs of a forceps maintaining the device in the coiled configuration.

As seen in FIG. 6, with the ring 10 maintained in its contracted configuration, the first vessel end 12a is drawn through the central opening 11, everted around the end of the ring and successively impaled on each of the protrusions 16r, 16m, 16a. Then as shown in FIGS. 7 and 8 the second vessel end 12b is drawn over the impaled first vessel end 12a and similarly successively impaled on each of the protrusions 16r, 16m, 16a, thereby apposing the intima 18 (interior surfaces) of the vessel ends. To complete the anastomosis, the device 10, having the two vessel ends 12a, 12b joined thereto, is expanded to its second (expanded) configuration as seen in FIG. 9 where it is maintained to hold the joined vessel ends in a slightly stretched state.

Figure 10B:
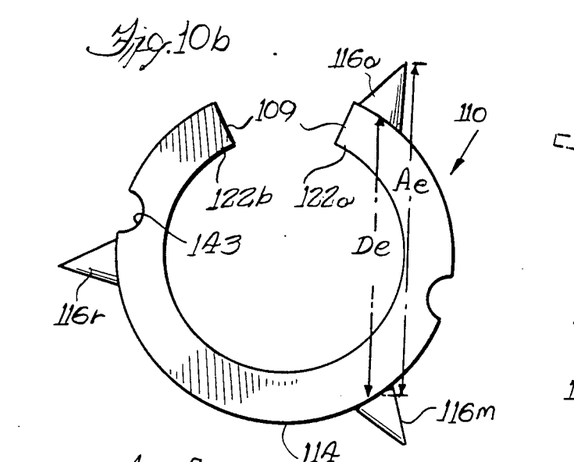
FIG. 10b is an end view of the device of FIG. 10a in a second expanded configuration.
Figure 11:
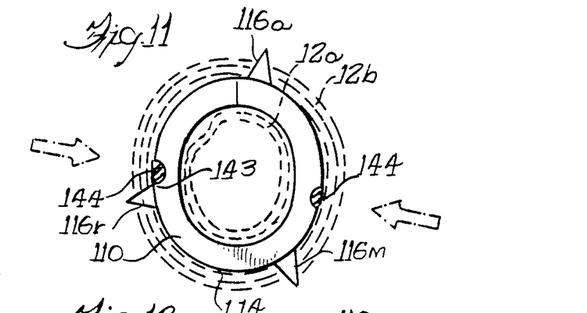
FIG. 11 is a side view of the coiled device of FIG. 10a with a pair of joined vessel ends shown in ghost.
Figure 12:
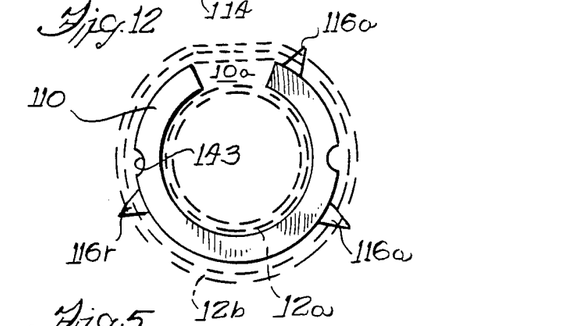
FIG. 12 is a side view of the expanded device of FIG. 10b with a pair of joined vessel ends shown in ghost.

By providing an incomplete ring 10 with a first coiled configuration for vessel end attachment and a second expanded configuration for vessel end healing, less stretching of the vessel wall is required when impaling the vessel ends on the protrusions 16, particularly the last protrusion, herein also referred to as the primary protrusion 16a. The device 10 is constructed so that in its expanded configuration (FIG. 2b) it is substantially annular, and for purposes of discussion herein, the interior and exterior diameters of the device refer to the expanded configurations of the devices (FIGS. 2b, 10b). Although the devices 10, 110 may have more than three protrusions 16, in the interest of rapidly anastomosing vessels it is generally preferred to have no more than three protrusions, particularly for anastomosing smaller vessels, and the device 10, 110 are discussed herein primarily in terms of having three protrusions with the understanding that similar considerations apply to devices having different numbers of protrusions.

Herein, the ring 10 in its expanded configuration has an exterior surface diameter of 1.4 mm which is greater than that relaxed exterior diameter of 1.0 mm of the vessel ends. The ring is typically between about 1.05 and about 1.40 times larger than the exterior vessel diameter. The blood vessel proximal to the heart is used as the first vessel, i.e., the vessel end which is first attached to the ring 10, and the relative dimensions described herein relate to this first vessel. The inside surface diameter is proportioned according to the outside diameter and the necessary radial thickness of the device. Typically, the inside diameter of the ring is equal to or slightly smaller than the normal, relaxed exterior diameter of the vessel ends, thereby slightly constricting the first vessel end 12a in its passage through the opening 11. To avoid over-constricting the first vessel end 12a, in its passage through the ring, the interior diameter of the ring is preferably no smaller than about 0.7 times the relaxed exterior diameter of the vessel ends.

The points or protrusions 16 are sufficiently long to impale both the first and the second vessel ends 12a and 12b. Generally the protrusions 10 extend so that their tips 20 (FIG. 2a) lie along a circular locus between about 1.5 and about 2.0 times the relaxed exterior diameter of the vessel ends 12a, 12b to be attached to the ring or between about 1.4 and about 1.8 times the exterior diameter of the ring. On the prior art ring 10p with three evenly spaced protrusions 16rp, mp, ap, and with a vessel end impaled on two of these protrusions, a third of the vessel wall circumference must be stretched between the base of one of the protrusions 16mp along the outside surface of the ring 10p and the tip of the third protrusions 16ap a distance A' as seen as FIG. 1c. Distance A' is a function of a distance D', 120° along the ring as measured from the base of the second protrusion 16mp to the base of the third protrusion 16ap on the exterior surface 14p of the ring.

The devices 10, 110 of the present invention are proportioned as described above in their final expanded configuration; however, in its coiled configuration the distance $D_c$ (FIG. 2a) between the base of an outermost primary protrusion 16a and the base of a middle protrusion 16m, 120° along the ring (as determined according to its expanded configuration) is reduced relative to the final distance $D_e$ (FIG. 2b) between these two points in the final expanded configuration. The distance $A_c$ between the base of the middle protrusion 16m and the tip of the primary protrusion 16a in the contracted configuration relative to the distance $A_e$ in the final expanded configuration is correspondingly reduced. For purposes of this invention and to facilitate impaling of the vessel ends on the ring, $D_c/D_e$ is about 0.8 or less and preferably 0.7 or less. These ratios hold generally true for devices even though they have more than three protrusions, such that the protrusions will be less than 120° apart. For purposes of this invention, regardless of the number of protrusions, the distances $D_c$ and $D_e$ are the measurements from the base of a primary protrusion on the outside surface of the ring to a point 120° therefrom along (not through the gap) the outside surface of the ring, the measurement in degrees being according to the expanded configuration.

Figure 15:
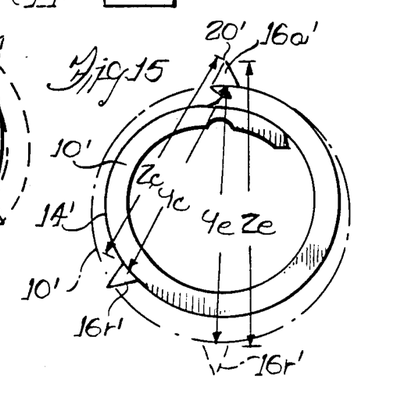
FIG. 15 is a side view of a two-protrusion variation of the device shown in FIGS. 2a and 2b, the coiled configuration being shown in solid and the expanded configuration being shown in ghost.

The ring 10', as in the embodiment shown in FIG. 15 (sheet 3), may contain as few as two protrusions, the exterior surface 14' of the ring being relied upon to cooperate with the protrusions in holding the stretched vessel ends therealong. In such case a distance $Y_c$ in the contracted configuration from the base of the primary protrusion 16a' to the base of the opposite or remote protrusion 16r' is less than about 0.7 and preferably less than about 0.6 times the distance $Y_e$ between the same two points in the expanded configuration. The distance $Z_c$ from the base of the remote protrusion 16r' to the tip of the primary protrusion 16a' is correspondingly reduced. The 120° distances described above hold true for this two-protrusion ring and the 180° distances hold true for three-protrusion rings.

Rings 10' having two protrusions have the important advantage of reducing the time for completing an anastomosis as compared to rings 10 having three or more protrusions. Furthermore, after a vessel end is impaled on one of the protrusions 16r', the stretching required to pull the vessel end over the tip 20' of the primary protrusion 16a' is distributed over a greater circumferential distance of the vessel end wall, i.e., 180° rather than 120° for a three-protrusion ring 10, minimizing the likelihood of vessel end tearing during the surgical procedure. However, if anatomical factors indicate that there would be any chance of the vessel ends slipping from along the exterior surface of the ring, for example, if the anastomosed vessel is subjected to substantial axial stress, rings having three or more protrusions are used.

Figure 3:
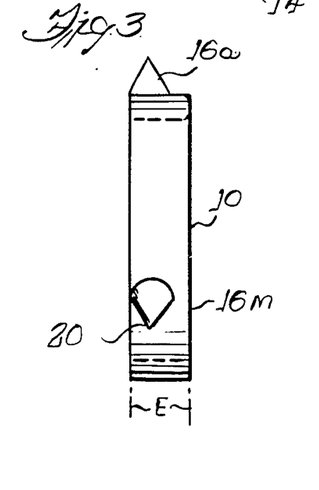
FIG. 3 is a side view of the device of FIG. 2.
Figure 4:
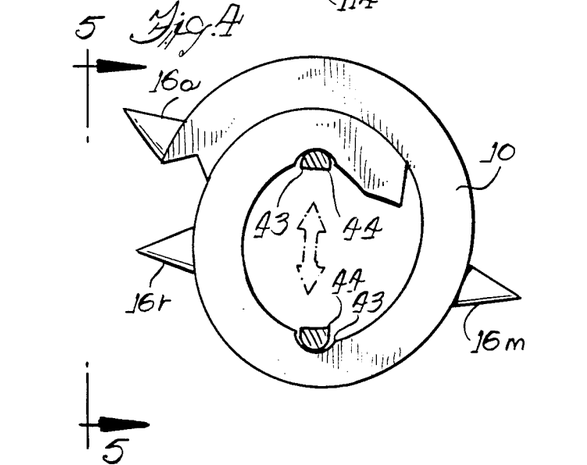
FIG. 4 (sheet 3) is an end view of a device, as shown in FIG. 2, showing the action of tangs of a reverse-action forceps in spreading the device from its coiled to its expanded configuration.
Figure 5:
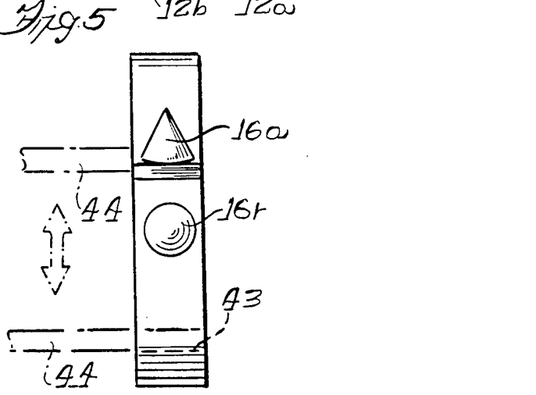
FIG. 5 (sheet 3) is a side view taken along line 5—5 of FIG. 4.

The face-to-face dimension of the ring 10 (distance E, FIG. 3) is not considered to be particularly critical. Typically the face-to-face dimension E of the ring is in the range of the radial thickness of the ring, e.g., between about 0.5 and about 2.0 times the radial thickness of the ring.

Maximum benefit of ring contraction to a smaller size is afforded by the primary protrusion 16a being closely adjacent to one of the ends 22a of the ring 10 and the remaining protrusions 16m, 16r being evenly spaced along the ring. If one of the ends 22a is radially outward of the other end in the coiled configuration, as is the case in the FIG. 2a, 2b embodiment, the primary protrusion 16a (which will be the protrusion to which each vessel end is attached last) is disposed closely adjacent to this outermost or first end 22a. If, as in the case of the FIG. 10a, 10b embodiment, both ends 122a, 122b are equidistance from a radial center in the contracted configuration, the protrusion 116a disposed closest to a first end 122a (than a remote protrusion 16r is to a second end 122b) is considered to be the primary protrusion.

The device 10 illustrated in FIG. 2a is molded in the illustrated contracted position with the second end 22b coiled within the first end 22a. The device is molded from a material which is deformable, preferably resiliently so. Suitable biocompatible materials for forming the ring include, but are not limited to, polytetrafluoroethylene, Preferably, the device is formed of a material, such as polyglycolic acid, polylactic acid and mixtures thereof which slowly dissovle within the body, whereby after anastomosis and a healing period, the device disappears. The natural molded configuration of FIG. 2a is maintained as the vessel ends 12a, 12b are attached thereto.

As a means for spreading the ring 10b after the vessels are attached thereto, a pair of notches 43 are formed in the interior surface 13. The tangs 44 (FIGS. 4, 5, 7, 8) of a reverse-action forceps or the like are inserted into the notches and used to spread the ring to its expanded configuration.

As the means of maintaining the device in its expanded configuration, interlocking means 30a, 30b are provided at the first end 22a and at the second end 22b of the ring. In the illustrated embodiment, the interlocking means comprise a wedge 30b at the second end and a complementary mating groove 30a at the first end. The invention is intended to cover other forms or interlocking means, but the interlocking means, as the wedge-groove arrangement illustrated in FIGS. 2a, 2b, should be simple because of the small size of the ring and the molding requirements for producing such a small ring. Also, the surgeon typically will not be able to view the ends of the ring, which at the time of expansion of the ring and mating of the ring ends is covered by the vessel ends, requiring the surgeon to mate the ends of the ring by "feel".

In using the device 10 of FIG. 2a, 2b to anastomose a first vessel 12a end to a second vessel end 12b, the first vessel end is initially drawn through the central open 11, e.g., with a surgical forceps. The vessel end 12a is then drawn around the end of the ring and along the outside surface 14, and using the forceps, the vessel is impaled on the protrusion 16r that is remote along the ring (not across the gap between the ring ends) from the primary protrusion 16a.

At this time, the surgeon must exercise some judgement in estimating a location of the wall of the vessel end about 120° along the circumference from the first point of impalement and impale this point on the middle protrusion 16m. The surgeon must bear in mind that although the protrusions 16a, 16m, 16p are not evenly spaced in the coiled configuration of the ring, they will be evenly spaced in the expanded configuration. (Even spacing of the protrusions, though desirable, is not a strict requirement, and the invention is intended to cover expandable devices in which the spacing between protrusions deviates from regularity.) The surgeon then locates a point of impalement of the vessel end an additional 120° along the circumference for impalement on the primary protrusion 16a. Because the distances $A_c$ is forshortened due to ring contraction, there is little chance that the wall of the vessel end will be torn during this operation. At this time, the first vessel end 12a is firmly attached to the device 10 as seen in FIG. 6, but the portion 17 of the vessel wall between the primary protrusion 16a and the remote protrusions 16r is somewhat slack. The intima 18 of the everted first vessel end 12a faces outward along the outside of the ring 10.

The second vessel end 12b is then drawn over the everted first vessel end 12a and sequentially impaled on the remote protrusion 16r, the middle protrusion 16m and the primary protrusion 16a, making sure that the impalation points are approximately 120° apart. The vessel ends 12a, 12b assume the configuration shown in FIG. 7.

Next, as shown in FIGS. 7 and 8, the surgeon inserts the tangs 44 of the reverse-action forceps in the notches 43 in the interior surface 13 of the ring 10 and expands the ring until the first and second ends 22a, 22b spread apart. With a compression of the reverse action forceps followed by release of the forceps, the interfitting means 30a, 30b at the ends 22a, 22b of the ring engage, locking the ring into its expanded configuration with the vessel ends permanently anastomosed as shown in FIG. 9. The intima 18a, 18b of the vessel ends are held by the ring 10 in sealing apposition during healing, and the relatively rigid device helps to maintain patency at the anastomosis site.

The device or ring 110 illustrated in FIGS. 10a and 10b also provides foreshortening of distance $D_c$ relative to distance $D_e$ and corresponding foreshortening of distance $A_c$ relative to distance $A_e$. In this case, however, the device 110 is molded in its expanded configuration (FIG. 10b), of which the ring itself comprises less than a complete annulus, e.g., between about 270° and about 330° of an annulus, leaving a small gap 109 between the first and second ends, 122a, 122b of the ring. The contracted configuration in this case is the stressed position shown in FIG. 10a with the first end 122a held in abutment against the second end 122b, e.g., with tangs 144 of a forceps. As a means of maintaining the ring 110 in the coiled position as the vessel ends are impaled on the protrusions, notches 143 that are generally diametrically opposed are formed in the exterior surface 114 of the ring for engagement with forceps tangs or the like. After the vessel ends are joined, release of the ring 110 causes it to spring to its expanded configuration where the natural molded shape of the ring maintains the position.

Again, with the ring 110 maintained in its coiled configuration, the first vessel end 12a is drawn through the central opening 111, everted around the end of the ring and successively impaled on the remote protrusion 116p, the middle protrusion 116m and the primary protrusion 116a at approximately equally spaced circumferential locations on the wall of the vessel. Next, the second vessel end 12b is drawn over the everted first vessel end 12a to appose their initima 118, and the second vessel end 12b is successively impaled on the remote protrusion 116r, the middle protrusion 116m and the primary protrusion 116a taking care to impale the vessel wall at evenly spaced circumferential locations. Finally, the ring 110 is released from the grip of the forceps, whereupon it assumes its unstressed expanded configuration, completing the anastomosis. Although the illustrated ring 110 has three protrusions, it may have only two protrusions or it may have more than three protrusions. In all cases, the reduction in 120° distances and 180° distances, described above, apply.

Figures 13, 14:
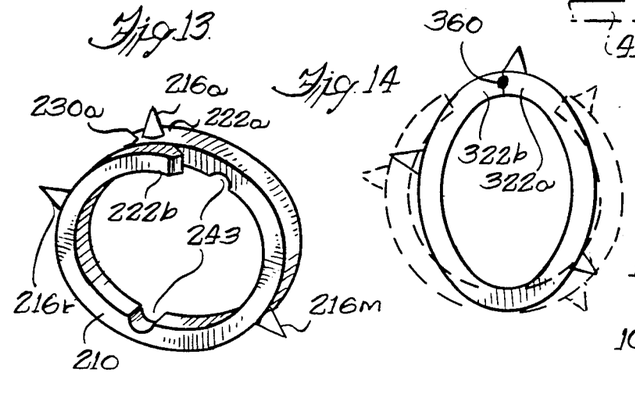
FIG. 13 is a perspective view of a further alternative embodiment of an anastomosis device according to the present invention.
FIG. 14 is a side view of a still further embodiment of an anastomosis device according to the present invention, the coiled configuration being shown in solid and the expanded configuration being shown in ghost.

Illustrated in FIG. 13 is an alternative embodiment of a device or ring 210 in which the molded configuration is the contracted state. In this case, the ends 222a, 222b are coiled out of plane so that they align side-by-side. A primary protrusion 216a is at one end 222a of the coiled device, and the ring has two other protrusions 216m and 216r. An interlocking groove 230a and wedge 230b at the ends of the ring serve to maintain or lock the ring in an expanded, planar configuration. Whereas the groove 30a and wedge 30b run in the axial direction in the FIG. 2a, 2b ring to resist the direction of natural contraction, the groove 230a and wedge 230b in the FIG. 13 embodiment run in the radial direction as befits the tendency of the ends of the ring to shift axially in the expanded configuration. To facilitate expanding the ring and bringing it into a coplanar configuration, notches 243 are molded into the side of the ring for receiving prongs of a forceps-like surgical tool.

Illustrated in FIG. 14 is an alternative embodiment of a ring 310 which is molded in an expanded configuration. In this case, subsequent to molding, the ends 322a, 322b are brought into abutment, and a frangible interlocking means 360 such as a "weld" is formed between the ends which holds the ring in its stressed, coiled configuration but is easily disconnected as by being broken or cut during surgery to allow the ring to assume its unstressed, expanded configuration after the vessel ends are impaled on its protrusions 316. Such a weld 360 may be formed with a small amount of biocompatible material or might be formed by melting a superficial portion of the ends together.

EXAMPLE 1

A ring 10, structured as described in reference to the FIG. 2a, 2b embodiment is adapted for suturing ends of a 1 mm exterior diameter vessel. The ring is formed of polyglycolic acid and is proportioned as follows. The ring (in its expanded configuration) has a 1.00 mm interior diameter, a 1.4 mm exterior diameter and an face-to-face (axial direction) thickness E of 0.1 mm. Three protrusions 16 each extend 0.4 mm outward of the external wall of the ring. The distance $D_c$ between the base of the middle protrusion 16m and the tip of the primary protrusion 16a in the unstressed coiled configuration is 1.0 mm and the corresponding distance $D_e$ in the expanded configuration is 1.4 mm. The distance between the tip of the middle protrusion 16 and the tip of the protrusion 16r in the coiled configuration is 1.5 mm and the corresponding distance in the expanded configuration is 1.7 mm. The distance between the protrusion tips 16r and 16a in the coiled configuration is 1.25 mm and in the expanded configuration is 1.7 mm.

A male Sprague-Dawley rat weighing 230 grams is anesthetized with intraperitoneal pentobarbital, and the cartoid artery is exposed. The exterior vessel diameter is about 1.0 mm measured prior to arterial isolation to avoid diameter variation induced by spasm or dilation due to smooth muscle relaxation by topical lidocaine.

The sutureless ring 10 is used to rejoin the severed artery. A forceps is used to draw the end of the first vessel end 12a through the opening 11 in the ring 10, evert the first vessel end 12a and impale the vessel end on each of the three protrusions 16r, 16m, 16p. Then the surgeon uses the forceps to similarly impale the other vessel end 12b on the protrusions 16r, 16m, 16p so as to appose the intima of the ends of the vessels. Finally, the surgeon inserts the tangs of a reverse-action forceps into the notches of the ring and expands the ring until the wedge at one end of the ring snaps into the grove at the other end, completing the anastomosis with the vessel ends held in fluid-tight apposition. The entire anastomosis procedure is performed in about one minute, an extremely short time for this type of procedure. The anastomosis proves to be patent, i.e., it remains open to the flow of blood therethrough.

EXAMPLE 2

A ring 110, structured as described in referenced FIG. 10a, 10b embodiment is adapted for suturing a 1 mm outside diameter vessel. The ring is formed of polyglycolic acid and is proportioned as follows. The ring has a 1.0 mm interior diameter, a 1.4mm exterior diameter and a face-to-face (axial direction) E thickness of 0.1 mm. Three protrusions 116 each extend 0.4 mm outward of the external wall of the ring. The distance $D_c$ between the tip of the middle protrusion 116m and the base of the primary protrusion 116a in the unstressed coiled position is 0.9 mm and the corresponding distance $D_e$ in the expanded configuration is 1.2 mm. The distance $A_c$ between the base of the middle protrusion and the tip of the primary protrusions in the coiled position is 1.0 mm and the corresponding distance $A_e$ in the expanded configuration is 1.4 mm.

A male Sprague-Dawley rat weighing 230 grams is anesthetized with intraperitoneal pentobarbital, and the cartoid artery is exposed. The exterior vessel diameter is about 1.0 mm measured prior to arterial isolation to avoid diameter variation induced by spasm or dilation due to smooth muscle relaxation by topical lidocaine.

The suturless ring is used to rejoin the severed artery. A second forceps is used to draw the end of the first vessel through the opening in the ring 20, evert the vessel 12 and impale the vessel end on each of the three protrusions. Then the surgeon uses the second forceps to similarly impale the other vessel end on the protrusions so as to appose the intima of the ends of the vessels. Finally, the surgeon slips the tangs of the first forceps from the notches of the ring allowing the ring to expand, completing the anastomosis with the vessel ends held in fluid-tight apposition.

The size of the cartoid artery anastomised in the above examples is similar in size to the type of blood vessels which must be anastomosed in many human microsurgical procedures, such as reconstruction of an injured hand or an amputated finger or hand. This rat vessel is similar in strength and resistance to tearing to many human vessels of corresponding size, and therefore, it is feasible to similarly anatomose a human vessel.

The anastomoses performed in the above Examples are end-to-end anastomoses in which a first vessel end is anastomosed to a second vessel end. Generally in such anastomosis procedures, the two vessel ends are about the same diameter. If the vessel ends are of somewhat different diameters, the ring size is selected according to the diameter of the smaller vessel and the smaller vessel end is the end initially drawn through and everted around the ring and the larger vessel end is then tented and hooked thereover. The devices described herein may also be used for effecting an end-to-side anastomosis in which a vessel end is drawn through, everted and hooked to the ring and then a second vessel having a prepared opening in its sidewall of a diameter generally equal to the lumen of the first vessel end is draped over the everted first vessel end and impaled on the protrusions.

While the invention has been described in terms of a preferred embodiment, modifications obvious to one with ordinary skill in the art may be made without departing from the scope of the invention.

Various features of the invention are set forth in the following claims.

What is claimed:

1. An anastomosis device for interconnecting the ends of first and second living vessels without tearing the same, said device comprising:
    a ring-like body of biologically compatible material having flexibility to change its shape between a smaller size at a contracted state and a larger size at an expanded state,
    said ring-like body being split and having separable ends,
    a plurality of points on the ring-like body for impaling the ends of the first and second living vessels in apposition on the exterior of the ring-like body.
    said ring-like body being biased to one of said states and being moved by the surgeon to the other of its states.
    a first of said points being a primary point located adjacent one of said separable ends and being at a predetermined distance relative to a second remote one of said points when the ring-like body is in its contracted state, said remote point adapted to be impaled before the primary point, said primary point moving with the adjacent end to a distance greater than said predetermined distance and being the last of the points to be impaled prior to the ring-like body moving to its expanded state.

2. An anastomosis device in accordance with claim 1 in which locking means are provided on the ring-like body to lock the body in its expanded state after the surgeon has shifted the body from its biased, contracted state to prevent return to the contracted state.

3. An anastomosis device in accordance with claim 1 in which holding means on said ring-like body assist in holding the ring-like body in its contracted state and in which the ring-like body is biased to its expanded state.

4. An anastomosis device in accordance with claim 3 in which said holding means comprises a frangible member which is broken to release the body to resiliently expand to its expanded state.

5. An anastomosis device in accordance with claim 3 in which the holding means comprises means on the ring-like body for gripping by a surgeon's tool to contract the ring-like body to its contracted state.

6. An anastomossis device in accordance with claim 1 in which the ring-like body has separable ends abutted together to form a completed ring in one of its states and in which the ends are separated when the ring-like body is in the other of its states.

7. An anastomosis ring for joining the prepared ends of first and second living vessels without tearing the same, said ring comprising:
    a body of biocompatible material having a completed ring shape in one of its states,
    said body having a plurality of points on the exterior of the ring and over which the first and second vessel ends are extended for being impaled thereon,
    said ring body being shiftable between a smaller size contracted state for decreasing the extent of vessel elongation for impaling on said points and a larger size expanded state increasing the lumen size of the vessel ends on the ring,
    said body being split in one of its state with ends of the ring being separated and in the other of its states having the ends of the ring abutted to complete the ring,
    a first of said points being a primary point located adjacent one of said split ends and being at a predetermined distance relative to a second remote one of said points when the ring-like body is in its contracted state, said remote point adapted to be impaled before the primary point, said primary point moving with the adjacent end to a distance greater than said predetermined distance and being the last of the points to be impaled prior to the ring-like body moving to its expanded state.

8. An anastomosis ring in accordance with claim 7 in which the ring is resiliently biased to its contracted state with the ends of the ring separated, and interlocking means on the separated ends to interlock the ring ends when abutted and holding the ring in its expanded state.

9. An anastomosis ring in accordance with claim 7 in which the ring is resiliently biased to its expanded state with the ends of the ring being separated, and interlocking means joining the ends to hold the ring ends together until released for expansion.

10. Apparatus for anastomosing a prepared first living vessel end to a prepared second living vessel end without tearing the same comprising
   a substantially encircling member in the form of an incomplete ring having an interior surface, an exterior surface, a first ring end and a second ring end, said member being deformable between a first coiled configuration and a second expanded configuration,
   two or more protruding means extending radially outward of said exterior surface for impaling said living vessel ends,
   first means for maintaining said encircling member in said first configuration as said vessel ends are manipulated along said outside surface and impaled on said protruding means, and
   second means for subsequently maintaining said encircling member in said second configuration with said vessel ends impaled on said protruding means and thereby held along said exterior surface.
   a first of said points being a primary point located adjacent said first ring end and being at a predetermined distance relative to a second remote one of said points when the ring-like body is in its contracted state, said remote point adapted to be impaled before the primary point, said primary point moving with the adjacent end to a distance greater than said predetermined distance and being the last of the points to be impaled prior to the ring-like body moving to its expanded state.

11. Apparatus according to claim 10 wherein said first maintaining means comprises the natural unstressed molded configuration of said encircling member and said second maintaining means comprises interengaging mechanical means at said first and second ends for locking said encircling member into said second configuration.

12. Apparatus according to claim 10 wherein said second maintaining means comprises the natural unstressed, molded configuration of said encircling member with said first and second ends spaced apart.

13. Apparatus according to claim 10 wherein one of said protruding means is disposed closely adjacent to said first ring end.

14. Apparatus according to claim 10 wherein said first ring end in said first coiled position is radially outward of or radially equidistant relative to said second ring end, one of said protruding means is as close to said first ring end as any other of said protruding means is to said second ring end, and the linear distance between the outside surface at the base of said one protruding means to a point 120° along the exterior surface of the ring therefrom, is in the coiled configuration about 0.8 or less times the distance of between the same two points in the expanded configuration.

15. Apparatus according to claim 14 wherein said one protruding means is disposed substantially at said first end.

16. Apparatus according to claim 10 wherein said first ring end in said first coiled position is radially outward of or radially equidistant relative to said second ring end, one of said protruding means is as close to said first ring end as any other of said protruding means is to said second ring end, and the linear distance between the outside surface at the base of said one protruding means to a point 180° along the exterior surface of the ring therefrom, is in the coiled configuration about 0.7 or less times the distance between the same two points in the expanded configuration.

17. Apparatus according to claim 16 wherein said one protruding means is disposed substantially at said first end.

18. A method of anastomosing a prepared first living vessel end to a prepared second living vessel end without tearing the vessel ends comprising
   providing a substantially encircling member in the form of an incomplete ring having an interior surface, an exterior surface, a first ring end and a second ring end, said member being deformable between a first coiled configuration and a second expanded configuration, a primary and a remote protruding means for impaling said living vessel ends to hold them along said exterior surface, said primary protruding means being located closely adjacent to said first end, first means for maintaining said encircling member in said first, coiled configuration as said vessel ends are manipulated along said exterior surface and impaled on said protruding means, and second means for subsequently maintaining said encircling member in said second, expanded configuration with said vessel ends impaled along said exterior surface,
   while maintaining said member in said first configuration, extending said first vessel end through said encircling member, everting said first vessel end along said exterior surface and impaling said frist vessel end first on said remote protruding means and then on said primary protruding means, and then extending said second vessel end over said everted first vessel end to bring their intima into sealing apposition and impaling said second vessel end first on said remote protruding means and then on said primary protruding means and
   subsequently expanding said encircling member and maintaining the same in said second, expanded configuration.

19. Apparatus for anastomosing a prepared first living vessel end to a prepared second living vessel end comprising
   a substantially encircling member in the form of an incomplete ring having an interior surface, an exterior surface, a first ring end and a second ring end, said member being deformable between a first coiled configuration and a second expanded configuration,
   two or more protruding means extending radially outward of said exterior surface for impaling said living vessel ends,
   first means for maintaining said encircling member in said first configuration as said vessel ends are manipulated along said outside surface and impaled on said protruding means, and second means for subsequently maintaining said encircling member in said second configuration with said vessel ends impaled on said protruding means and thereby held along said exterior surface, said first maintaining means comprising the natural unstressed molded configuraton of said encircling member, said second maintaining means comprising interengaging mechanical means at said first and second ends for locking and encircling member into said second configuration, and said member having notch means along its interior surface for interfitting with tangs of a member-expanding surgical tool.

20. Apparatus for anastomosing a prepared first living vessel end to a prepared second living vessel end comprising a substantially encircling member in the form of an incomplete ring having an interior surface, an exterior surface, a first ring end and a second ring end, said member being deformable between a first coiled configuration and a second expanded configuration, two or more protruding means extending radially outward of said exterior surface for impaling said living vessel ends, first means for maintaining said encircling member in said first configuration as said vessel ends are manipulated along said outside surface and impaled on said protruding means, and second means for subsequently maintaining said encircling member in said second configuration with said vessel ends impaled on said protruding means and thereby held along said exterior surface, said second maintaining means comprising the natural unstressed, molded configuration of said encircling member with said first and second ends spaced apart, said first maintaining means comprising notch means along the exterior surface for interfitting with tangs of a surgical tool useful for coiling said member.

* * * * *

UNITED STATES PATENT AND TRADEMARK OFFICE
CERTIFICATE OF CORRECTION

PATENT NO. : 4,693,249

DATED : September 15, 1987

INVENTOR(S) : Robert R. Schenck and Harry P. Weinrib

It is certified that error appears in the above-identified patent and that said Letters Patent is hereby corrected as shown below:

On the Title Page:

FACE, OTHER PUBLICATIONS, Change "Fksperim" to --Eksperim

Column 1, Line 7, Change "anastomeses" to --anastomoses--.

Column 1, Line 24, Change "anasotomosing" to --anastomosing--.

Column 1, Line 51, After "Pat." insert --Specification--.

Column 1, Line 61, Change "or" to --of--.

Column 2, Line 1, Change "153-59" to --1, 53-59--.

Column 4, Line 19, Change "mp" to --16mg,--.

Column 4, Line 19, Change "ap" to --16ap,".

Column 4, Line 44, Change "device" to --devices--.

Column 5, Line 19, Change "complete" to --completed--.

Column 6, Line 16, Change "device" to --devices--.

Column 6, Line 22, Change "that" to --the--.

Column 6, Line 48, Change "mp, ap," to --16mp, 16ap,--.

Column 8, Line 4, Change the comma "," (first occurrence) to --.-- (period).

UNITED STATES PATENT AND TRADEMARK OFFICE
CERTIFICATE OF CORRECTION

PATENT NO. : 4,693,249

DATED : September 15, 1987

INVENTOR(S) : Robert R. Schenck and Harry P. Weinrib

It is certified that error appears in the above-identified patent and that said Letters Patent is hereby corrected as shown below:

Column 9, Line 8, After "reverse", insert -- - -- (hyphen).

Column 9, Line 46, Change "initima" to --intima--.

Column 10, Line 58, Change "grove" to --groove--.

Column 11, Line 21, Change "suturless" to --sutureless-.

Column 11, Line 32, Change "anastomised" to --anastomosed--.

Column 11, Line 39, Change "anatomose" to anastomose--.

Column 13, line 15, After "comprising" add -- : -- (colon).
Column 13, line 32, Change "." (period) to --,-- (comma).
Column 14, Line 20, After "comprising" add -- : -- (colon).

Column 14, Line 55, After "comprising" add -- : -- (colon).

Column 15, Line 9, change "and" to --said--.
Column 15, Line 17, After "comprising" add --:-- (colon).

Signed and Sealed this

Seventeenth Day of May, 1988

Attest:

DONALD J. QUIGG

Attesting Officer

Commissioner of Patents and Trademarks